United States Patent
King

(10) Patent No.: US 9,943,295 B2
(45) Date of Patent: Apr. 17, 2018

(54) METHODS AND SYSTEMS FOR MINIMALLY INVASIVE ENDOSCOPIC SURGERIES

(75) Inventor: Debra A. King, New York, NY (US)

(73) Assignee: Debra King, New York, NY (US)

( * ) Notice: Subject to any disclaimer, the term of this patent is extended or adjusted under 35 U.S.C. 154(b) by 677 days.

(21) Appl. No.: 13/185,364

(22) Filed: Jul. 18, 2011

(65) Prior Publication Data

US 2012/0016194 A1 Jan. 19, 2012

Related U.S. Application Data

(60) Provisional application No. 61/420,092, filed on Dec. 6, 2010, provisional application No. 61/365,319, filed on Jul. 17, 2010.

(51) Int. Cl.

| A61B 1/00 | (2006.01) |
|---|---|
| A61B 17/00 | (2006.01) |
| A61B 18/18 | (2006.01) |
| A61B 1/313 | (2006.01) |
| A61B 17/11 | (2006.01) |
| A61B 17/32 | (2006.01) |

(Continued)

(52) U.S. Cl.
CPC .... *A61B 17/00008* (2013.01); *A61B 1/00135* (2013.01); *A61B 1/00137* (2013.01); *A61B 1/313* (2013.01); *A61B 17/0218* (2013.01); *A61B 17/11* (2013.01); *A61B 17/3423* (2013.01); *A61B 18/14* (2013.01); *A61B 2017/1107* (2013.01); *A61B 2017/22067* (2013.01); *A61B 2017/320044* (2013.01); *A61B 2017/320056* (2013.01); *A61B 2018/00404* (2013.01); *A61B 2018/00595* (2013.01); *A61B 2217/005* (2013.01); *A61B 2217/007* (2013.01); *A61M 1/3655* (2013.01)

(58) Field of Classification Search
CPC ...... A61B 17/00008; A61B 17/320016; A61B 2017/320044; A61B 2017/00778; A61B 2017/320064; A61B 17/00778
USPC ..... 600/104, 156, 157; 606/159, 190, 46, 48
See application file for complete search history.

(56) References Cited

U.S. PATENT DOCUMENTS 5,063,796 A 11/1991 Gennep
5,373,840 A * 12/1994 Knighton ...................... 600/106

(Continued)

OTHER PUBLICATIONS

International Search Report for International Application No. PCT/US2011/044399 dated Nov. 25, 2011.

(Continued)

*Primary Examiner* — Matthew J Kasztejna
*Assistant Examiner* — Rynae Boler
(74) *Attorney, Agent, or Firm* — Leason Ellis LLP

(57) ABSTRACT

Methods and systems are provided for harvesting at least a portion of a blood vessel, such as the radial artery in the upper extremity and the saphenous vein in the lower extremity. In certain embodiments, an endoscopic surgical system includes a blunt tip trocar (BTT) for insertion into an incision in the extremity, a cannula for insertion through the BTT, a bisector/bipolar device, and an endoscope. The endoscope may have a dissection tip at its distal end for dissecting tissue from the blood vessel and, with the tip removed, may provide a visual field at its distal end. The endoscope is sized to fit into the cannula and provides visualization of the blood vessel during bisection with the bisector/bipolar device.

16 Claims, 7 Drawing Sheets

(51) Int. Cl.

| | | |
|---|---|---|
| A61B 17/02 | (2006.01) | |
| A61B 18/14 | (2006.01) | |
| A61B 18/00 | (2006.01) | |
| A61M 1/36 | (2006.01) | |
| A61B 17/34 | (2006.01) | |
| A61B 17/22 | (2006.01) | |

(56) References Cited

U.S. PATENT DOCUMENTS

| | | | |
|---|---|---|---|
| 5,607,391 | A | 3/1997 | Klinger et al. |
| 5,899,884 | A * | 5/1999 | Cover et al. .............. 604/119 |
| 5,928,138 | A * | 7/1999 | Knight et al. ............. 600/201 |
| 6,042,538 | A * | 3/2000 | Puskas .................. A61B 1/018 600/114 |
| 6,951,568 | B1 | 10/2005 | Chin |
| 7,270,658 | B2 | 9/2007 | Woloszko et al. |
| 2002/0092533 | A1 | 7/2002 | Boyd et al. |
| 2002/0156348 | A1 * | 10/2002 | Schoellhorn ..... A61B 17/00008 600/164 |
| 2003/0216690 | A1 * | 11/2003 | Foley ....................... 604/119 |
| 2006/0217706 | A1 | 9/2006 | Lau et al. |
| 2006/0276815 | A1 * | 12/2006 | Lotti et al. ................ 606/159 |
| 2008/0161841 | A1 * | 7/2008 | Clague et al. ............. 606/159 |
| 2009/0023986 | A1 * | 1/2009 | Stewart et al. ............ 600/104 |
| 2009/0024121 | A1 | 1/2009 | Kasahara et al. |
| 2009/0281556 | A1 | 11/2009 | Newell et al. |
| 2012/0046677 | A1 * | 2/2012 | Lin et al. ................. 606/159 |

OTHER PUBLICATIONS

Paul, Eric M. et al.; Endoscopic basilic vein transposition for hemodialysis access; Journal of Vascular Surgery, Jun. 2010, pp. 1451-1456.

Hosam F. El Sayed, MD., et al.; Utility of Basilic Vein Transposition for Dialysis Access; Vascular. 2005; 13(5):268-274.

Woo, K., et al.; Evaluation of the efficacy of the transposed upper arm arteriovenous fistula: a single institutional review of 190 basilic and cephalic vein transposition procedures; J Vasc Surg. Jul. 2007; 46 (1):94-99; Abstract.

Torina, PJ, et al.; Brachial vein transposition arteriovenous fistula; is it an acceptable option for chronic dialysis vascular access?; J Vasc Access. Jan.-Mar. 2008; 9 (1); 39-44; Abstract.

Ramanathan, Anantha K., et al.; A retrospective review of basilic and cephalic vein-based fistulas; Vascular. Apr. 2011; 19 (2): 97-104; Abstract.

Woo, K., et al.; Comparison of the efficacy of upper arm transposed arteriovenous fistulae and upper arm prosthetic grafts; J Vasc Surg. Dec. 2009; 50 (1): 1405-11; Abstract.

Oliver, Matthew J., MD, MHS, et al.; Chronic hemodialysis vascular access: Types and placement; http://www.uptodate.com/contents/chronic-hemodialysis-vascular-access-types-and-placement.

C.H. Lin et al., A Modified Technique for Endoscopic Transposition of Upper Arm Basilic Vein in Autologous Arteriovenous Fistula Creation, Jan. 2006, Elseveir, EJVES Extra, vol. 11, pp. 7-9.

Bernardo D. Martinez et al., Transposition of the Basilic Vein for Arteriovenous Fistula: an Endoscopic Approach, Feb. 2001, Elsevier Science Inc., J Am Coll Surg, vol. 192, No. 2, pp. 233-236.

* cited by examiner

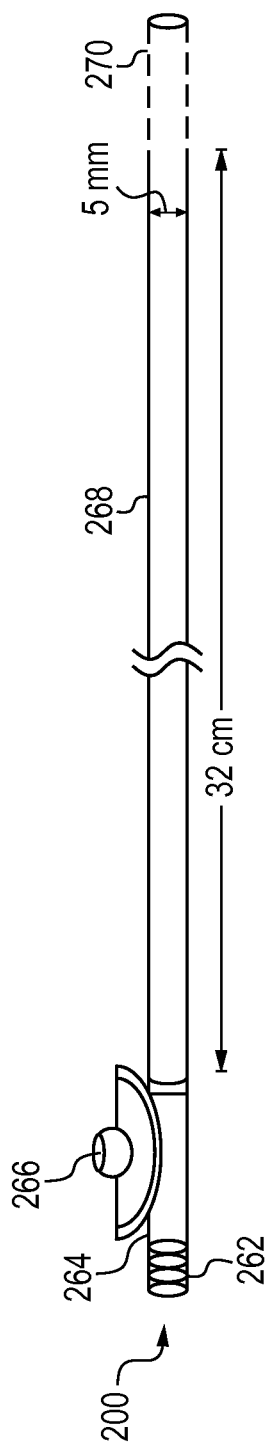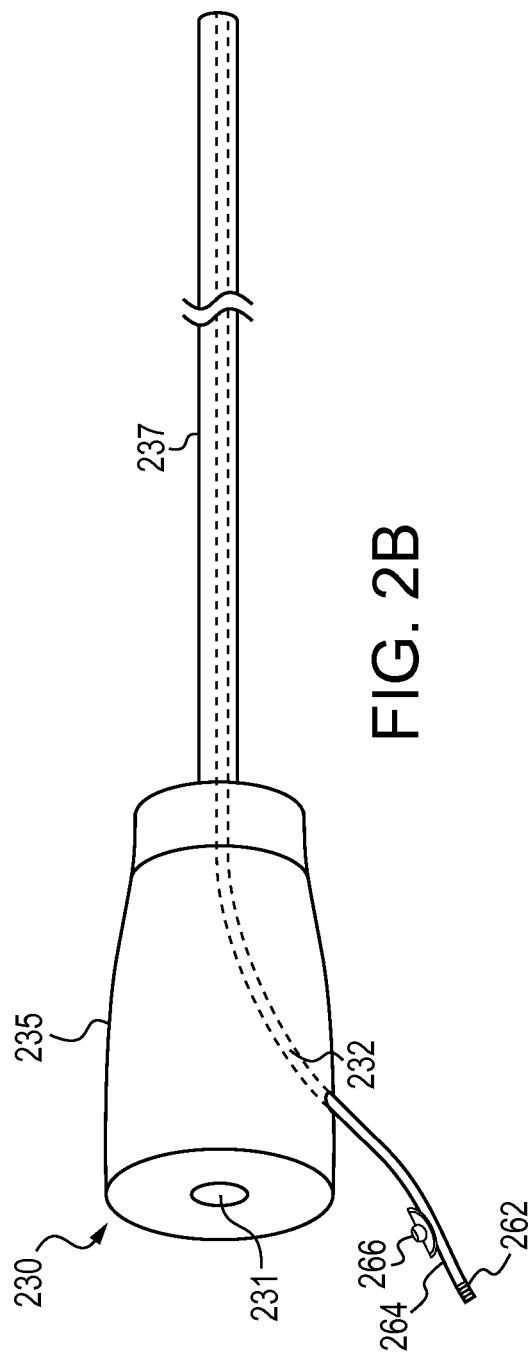
FIG. 2A
FIG. 2B

METHODS AND SYSTEMS FOR MINIMALLY INVASIVE ENDOSCOPIC SURGERIES

CROSS-REFERENCE TO RELATED APPLICATIONS

This application claims the benefit of, and priority to, U.S. Provisional Application No. 61/365,319, filed Jul. 17, 2010, entitled "Minimally Invasive Endoscopic Surgical Approach: Arterial Venous Fistula Ligation-Excision and Arterial Venous Fistula Creation with Simultaneous Transposition" and U.S. Provisional Application No. 61/420,092, filed Dec. 6, 2010, entitled "Methods and Systems for Minimally Invasive Endoscopic Surgeries," both of which are incorporated herein by reference in their entirety.

BACKGROUND

Minimally invasive surgery is the desired approach to reduce scarring, improve cosmesis, lessen postoperative pain, limit potential for infection, and promote faster recovery. Minimally invasive approaches have become the standard of care since laparoscopic cholecystectomy was introduced in the 1990s.

Traditional open techniques for certain surgical procedures, such as vascular access via arteriovenous fistulas for dialysis and/or fasciotomy, create long and/or multiple incisions and disfiguring scars. These open techniques place patients at high risk for infections, bleeding, painful surgical sites, poor wound healing, and/or functional impairment.

Thus, improved, minimally invasive endoscopic methods for arteriovenous fistula and/or fasciotomy surgeries, and improved surgical instrumentation for performance of those and other minimally invasive procedures, are needed.

SUMMARY

Embodiments of the present invention provide methods for minimally invasive endoscopic surgeries, including minimally invasive endoscopic arteriovenous (AV) fistula creation with simultaneous or staged transposition, minimally invasive endoscopic ligation and excision of aneurysmal AV fistulas, and minimally invasive endoscopic fasciotomy. Benefits of the methods described herein relative to traditional open techniques may include, for example, reduction in unsightly and disfiguring scarring at a long incision site, faster wound healing, reduced pain, lower infection risk, and elimination of a subsequent surgery.

Embodiments of the present invention also provide an improved surgical system designed to perform the surgical methods described herein and other minimally invasive endoscopic procedures, particularly useful for the upper extremities and smaller parts of the lower extremities. Benefits of the systems described herein relative to existing surgical instrumentation may include, for example, ease of use, reduced slippage, improved precision and results, and smaller surgical incisions.

Methods and systems of the present invention are directed to the harvesting of a blood vessel or a portion of a blood vessel, such as the radial artery in the upper extremity and the saphenous vein in the lower extremity. In certain embodiments, an endoscopic surgical system for use in endoscopically harvesting at least a portion of a blood vessel is provided. The system may include a blunt tip trocar (BTT) for insertion into an incision in the extremity, a cannula for insertion through the BTT, a bisector/bipolar attachment or device and an endoscope. The endoscope may have a dissection tip at its distal end for dissecting tissue from the blood vessel and, with the tip removed, may provide a visual field at its distal end. The endoscope is sized to fit into the cannula and provides visualization of the blood vessel during bisection with the bisector/bipolar device.

In other embodiments the system further includes an endoscopic suction device sized to fit into and extend to the distal end of the cannula to provide suction at the cannula distal end to remove debris without removing the cannula. The suction device may have a handle and a body sized to fit into the cannula, wherein the body is about 32 cm in length.

Methods of harvesting blood vessels endoscopically, without the need for an open surgery, including by using the aforementioned systems, are also disclosed. One such method for harvesting at least a section of a blood vessel from an extremity may include making an incision in the extremity sized to receive an endoscopic device (e.g., about 2 cm) and introducing an endoscope through the incision. The endoscope may have a dissector tip used for dissecting tissue around the blood vessel. An endoscopic device may then be introduced, including a harvesting cannula and the endoscope without the tip, with a bisector/bipolar device attachment. The bisector/bipolar device or attachment may be used to cut and cauterize branches of the blood vessel while under endoscopic visualization. A suction device introduced via the cannula in the incision may be used to suction away blood, irrigation fluid or other debris while the cannula is in situ. The section of the blood vessel may be harvested via a separate stab incision.

Additional features and advantages of embodiments of the present invention are described further below. This summary section is meant merely to illustrate certain features of embodiments of the inventions, and is not meant to limit the scope of the invention in any way. The failure to include, or the inclusion of, a specific feature or embodiment of any invention in this summary section should not be construed to limit any invention as claimed.

BRIEF DESCRIPTION OF THE DRAWINGS

The foregoing summary, as well as the following detailed description of the embodiments, will be better understood when read in conjunction with the appended drawings. For the purposes of illustrating the methods and systems of the present application, there are shown in the drawings preferred embodiments. It should be understood, however, that the application is not limited to the precise arrangements and instrumentalities shown. In the drawings:

FIG. 2 shows a suction device according to an embodiment of the invention. FIG. 2A shows the suction device alone and FIG. 2B shows the suction device inserted into the harvesting cannula of FIG. 1C.

DETAILED DESCRIPTION OF EMBODIMENTS

Endoscopic Surgical Systems

Figure 1A:
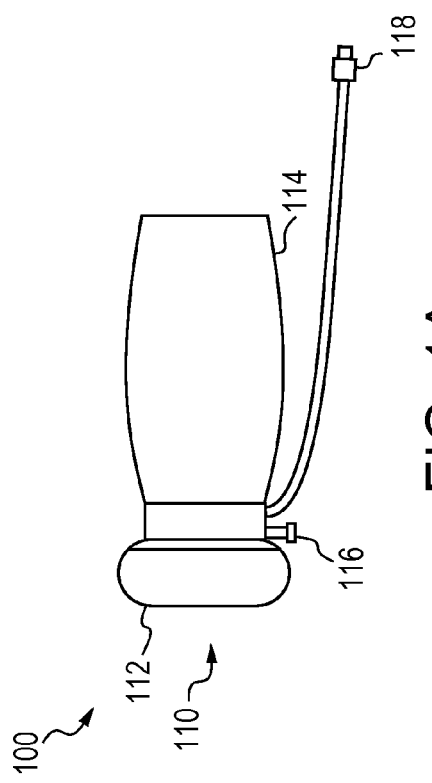
FIG. 1A shows a blunt tip trocar, FIG. 1B an endoscope, FIG. 1C a harvesting cannula, and FIG. 1D a bisector/bipolar device.

Existing endoscopic vein harvesting systems were developed for harvesting of the saphenous vein or radial artery as conduits for coronary artery bypass graft surgery. However, these and other endoscopic devices have been applied to limited types of procedures. In addition, the existing devices are large and cumbersome to maneuver, even for their intended cardiovascular-related uses.

The anatomy of the upper extremity, and nerve-vein differentiation, large peripheral vein branches, and less $CO_2$/less pressure in the upper extremity, are of particular technical consideration in the endoscopic AV fistula surgical procedures described herein. Minimizing damage to the intimal vein wall in transposition cases is of great importance. Thus, improved endoscopic devices, suitable for these and other minimally invasive applications, are needed.

An improved endoscopic system, which is smaller, more precise, and easier to use, as compared to existing endoscopic systems, is presented. Moreover, the improved endoscopic system described herein is particularly well-suited for minimally invasive endoscopic procedures in the upper extremity and/or smaller parts of the lower extremity, including, but not limited to, the novel minimally invasive endoscopic AV fistula, cardiovascular, and fasciotomy surgical methods described herein.

In some embodiments, the invention provides an endoscopic system 100 comprising a blunt tip trocar (BTT) introducer 110, an endoscope 120, a harvesting cannula 130, and a bisector/bipolar device 140, as shown in FIG. 1A-D. In some embodiments, the endoscopic system of the present invention includes a suction device 200, as shown in FIG. 2A-B.

Figure 3:
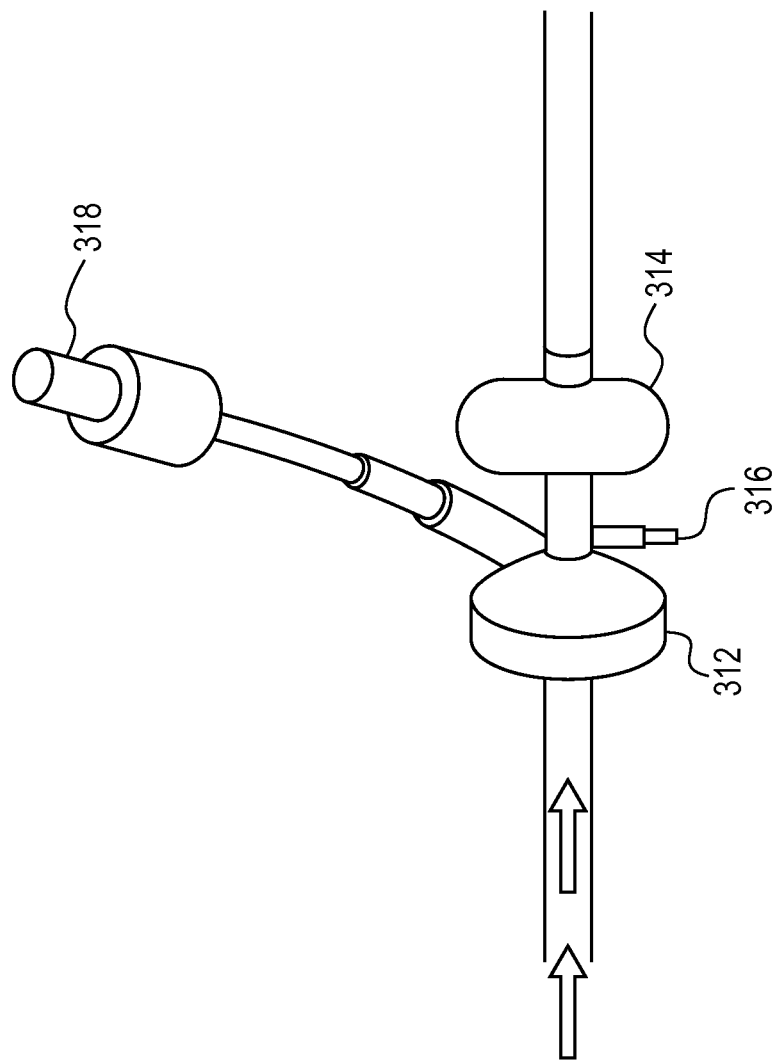
FIG. 3 shows a detailed view of the blunt tip trocar of FIG. 1A.

As shown in FIG. 1A, the BTT 110 may include an inflatable occlusion balloon 114, a balloon inflation port 116 (which may be attached to a syringe or other device for filling with air), a $CO_2$ port 118 (to access a constant low flow of $CO_2$, e.g., 8-10 mm Hg), and an endoscope/cannula seal 112 to create a sealed tunnel. FIG. 3 shows a detailed view of this element, according to some embodiments, with like features having similar numbering, and arrow indicating the insertion direction of the endoscope/cannula.

Figure 1B:
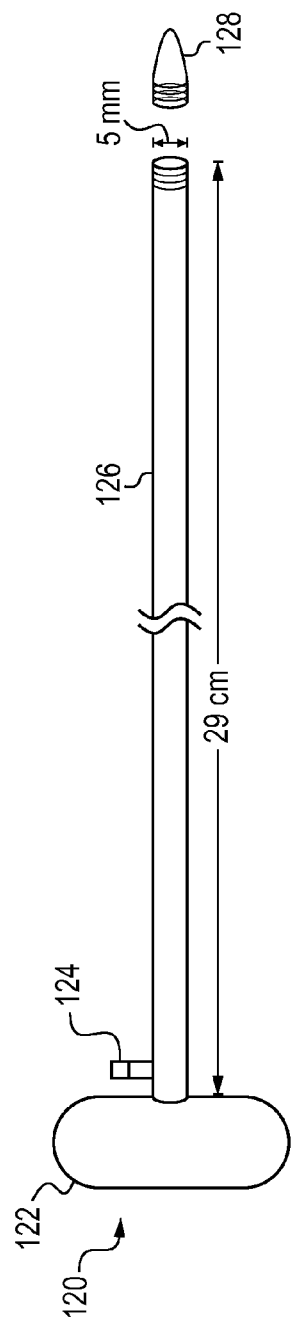
FIG. 1 shows an endoscopic system according to an embodiment of the invention.
Figure 1C:
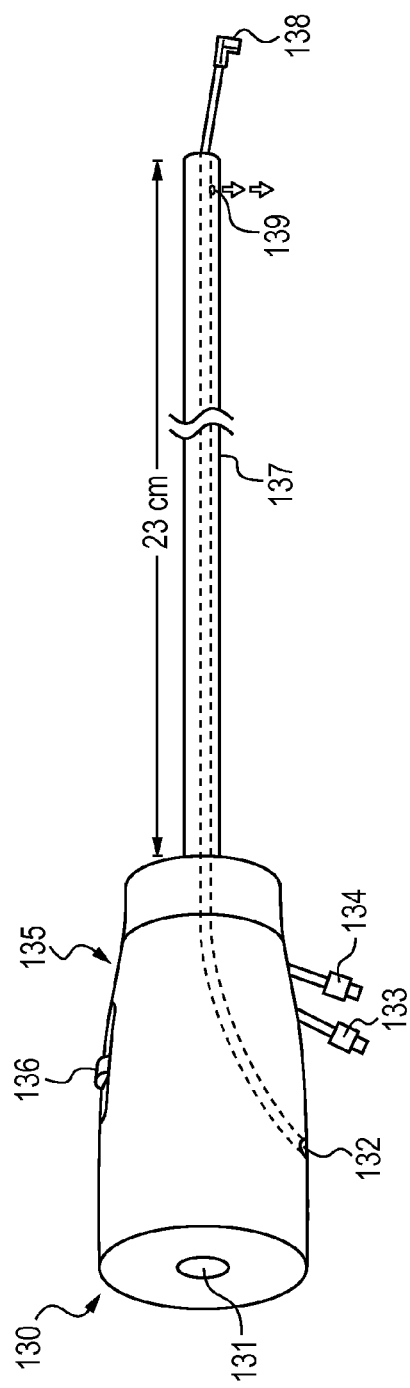
Figure 4:
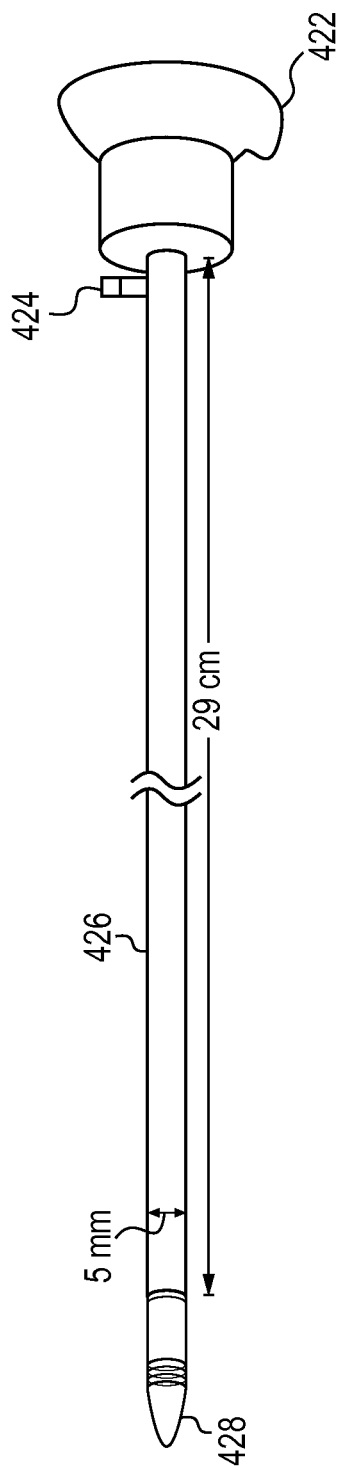
FIG. 4 shows a detailed view of the endoscope of FIG. 1B.

In some embodiments, a standard endoscope 120 may be used in the endoscopic system. An exemplary currently-available endoscope is a Storz endoscope. As shown in FIG. 1B, the Storz scope is preferably a 0° endoscope having a length 126 of about 26 cm to about 32 cm, preferably about 29 cm and a diameter/width of about 5 mm. The endoscope may include an attachable clear conical tip 128 for dissection at a distal end and a site for attachment of a camera head 122 at a proximal end. Other features of the endoscope may include, for example, an illumination port 124 and a light source and/or a camera. Another view of the endoscope is shown in FIG. 4, with like features having similar numbering. As shown in FIG. 1B-C, the endoscope may be inserted into the harvesting cannula through opening 131 at the proximal end. These two elements (endoscope and cannula) together are referred to herein as the endoscopic device.

Figure 5:
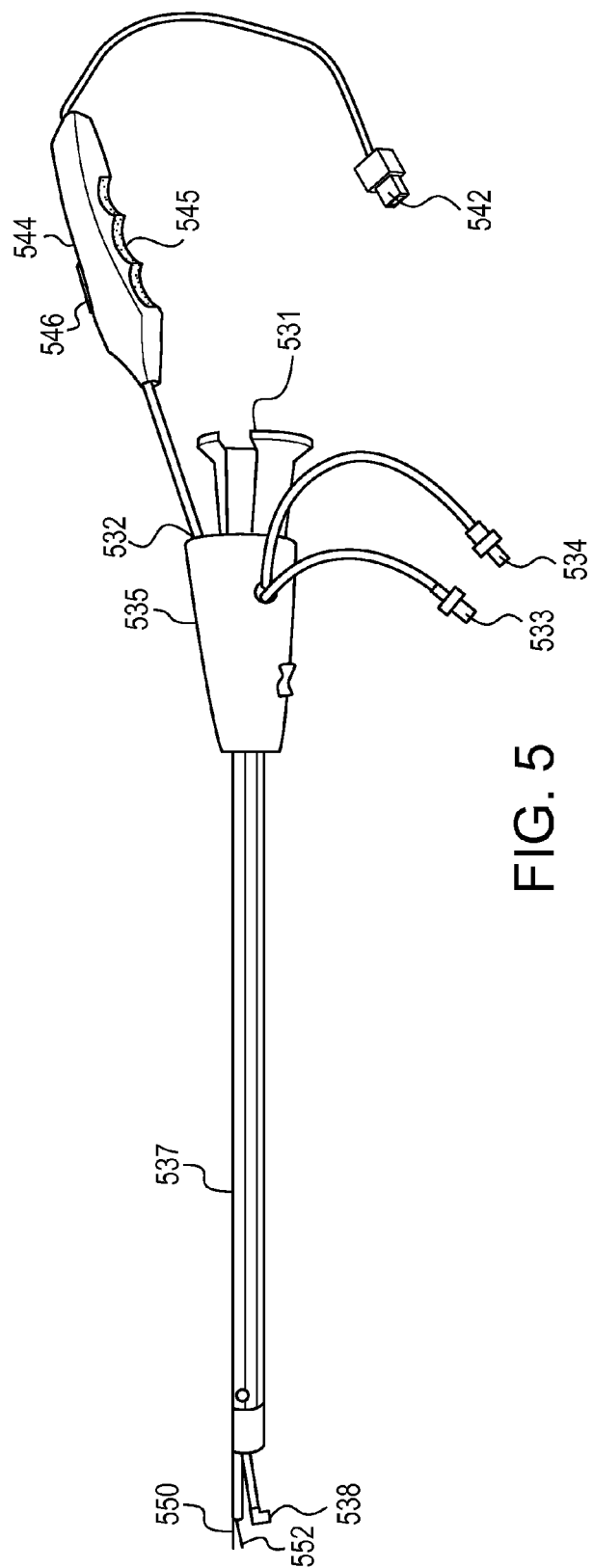
FIG. 5 shows a detailed view of the harvesting cannula of FIG. 1C with the bisector/bipolar device of FIG. 1D inserted.

Referring to FIG. 1C, the harvesting cannula 130 of the endoscopic system of the present embodiment preferably has a shaft 137 with a length equal to, or preferably less than, the length of the endoscope. For example, for use with an endoscope of length about 29 cm, as shown in FIG. 1B and FIG. 4, the cannula preferably has a shaft 137 length of about 20 cm to about 26 cm, preferably about 23 cm. In some embodiments, as shown in FIG. 1C, the cannula includes at its distal end (i.e., the end inserted into the incision site through the BTT) a C-ring 138 and one or more openings 139 for irrigation and/or $CO_2$ insufflation. At a proximal (non-inserted) end of the cannula, there is a handheld portion 135, which may, for example, have an adjustable slider 136 coupled to the C-ring for extending/retracting the C-ring, at least one port/opening 132 for inserting the bisector or the suction device, and/or one or more syringe attachments (e.g., for saline irrigation 133 and/or $CO_2$ insufflation 134). In some embodiments, the handheld portion 135 is about 14 cm in length. Other handle lengths and/or features for comfort, reduced slippage (e.g., for more stable use with wet gloves), and/or ease of use are contemplated. Preferably, the handheld portion 135 is ergonomically correct. FIG. 5 shows a view of the cannula 130 with bisector/bipolar device 140 inserted, according to an embodiment of the invention, with like features having similar numbering.

Figure 1D:
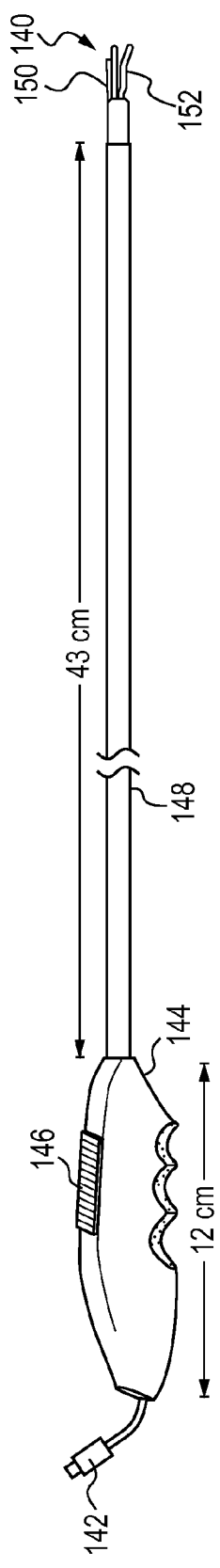
Figure 6:
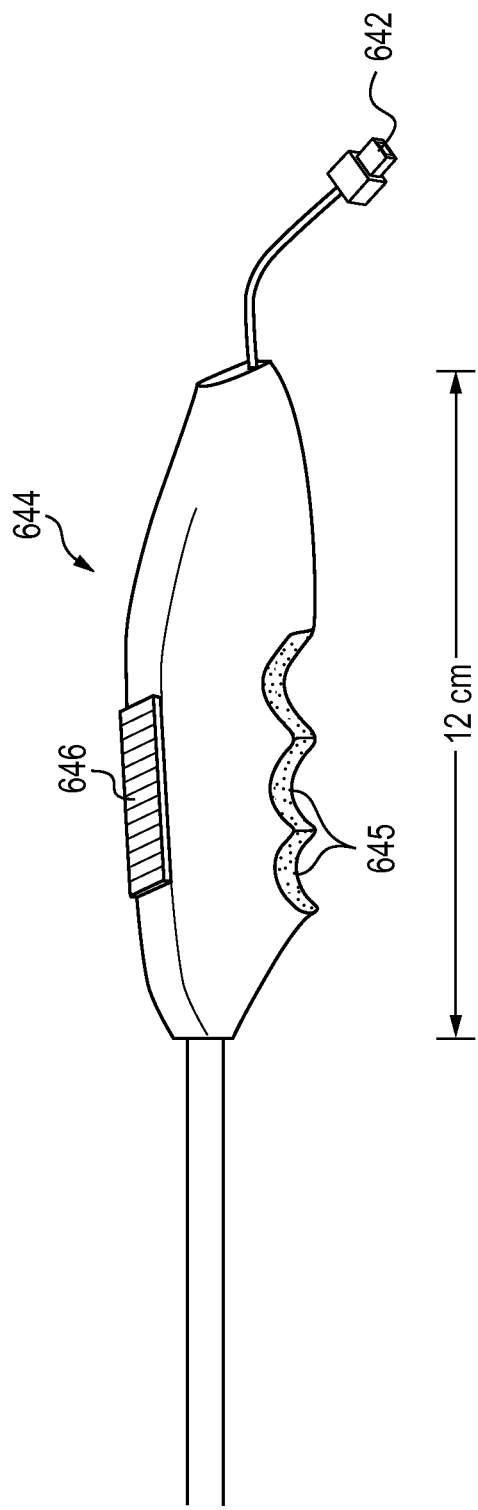
FIG. 6 shows a detailed view of the bisector/bipolar device of FIG. 1D, with an enlarged view of the handle.

Referring to FIG. 1D, in some embodiments, a bisector/bipolar device 140 (also referred to herein as the bisector) is used in the endoscopic system and can, for example, be inserted into the harvesting cannula through opening/port 132 as shown in FIG. 1C. The length 148 of the bisector/bipolar device is preferably related to, and may vary with, the length of the cannula used. The bisector/bipolar device is preferably longer than the harvesting cannula (e.g., long enough to extend through the distal end of the cannula to cut tissue, and sufficient on the proximal end to ensure that the handle does not dangle and bend, or come too close to the port 132). As shown in FIG. 1D, the bisector/bipolar device 140 is about 40 cm to about 46 cm, preferably about 43 cm, in shaft 148 length, when used with cannula 130. The bisector/bipolar device 140 may include a blade 150 and/or a cautery 152 at its distal end. The bisector/bipolar device 140 may also include at its proximal end a handle 144 with moveable slider 146 for actuating the scissors/cutting. The bisector handle preferably includes an electrical connector 142. In some embodiments, the bisector handle 144 is between about 11 cm and about 12 cm in length. As shown in FIG. 6, in certain embodiments, the bisector handle 644 may include, for example, three grooves 645 for fingers. Other handle lengths and/or features for comfort, reduced slippage (e.g., with wet gloves), ergonomic correctness, and/or ease of use are contemplated. For example, as shown in FIGS. 5 and 6, in some embodiments, the finger grooves 545/645 may be textured (e.g., with small raised semispherical bumps) and/or comprise a non-slip material (e.g., a rubber, silicone, or other grip material). Such a handle can prevent the slipping and spinning that can easily occur during surgical procedures using an existing, smooth-handled bisector/bipolar device.

Referring to FIG. 2A-B, in some embodiments, a suction device 200 is used in the endoscopic system, and can, for example, be inserted into the harvesting cannula 230 through a port 232, as shown in FIG. 2B. In some embodiments, the port 232 for the suction device is the same port 132 that is used for the bisector device. The length 268 of the suction device is preferably related to, and may vary with, the length of the cannula used. For example, the length of the suction device should be sufficient to extend through the harvesting cannula and out the distal end to suction out contents, and be sufficient on the proximal end for ease and safety of use (e.g., not too long/dangling around or too short/hugging the endoscopic device). The suction device 200 is about 29 cm to about 35 cm, preferably about 32 cm, in shaft 268 length, when used with cannula 130. In some embodiments, however, the suction device may be the same length as the bisector device (e.g., about 43 cm), for example so that it may be used in conjunction with an existing cannula, which is larger than cannula 130. The suction device 200 may include a handle 264 at its proximal end. In some embodiments, the suction device handle 264 is about 5 cm. In some embodiments, the suction device 200 is optionally fenestrated at its distal end 270 (e.g., the distal 2 cm). In some embodiments, the suction device 200 includes a proximal-end connector 262 to wall suction tubing, which connects off the sterile field to a suction canister. A thumb hole or other controllable valve/opening 266 (e.g., a screw valve) may be provided at the proximal end to turn on/off and/or vary the amount of suction. Suction device 200 allows the endoscopic field of vision to be cleared (e.g., of blood, debris, and/or fluid used to wash the endoscope) by suction, without deflating the BTT 110 and removing the endoscopic device, as is traditionally done in the types of endoscopic surgeries discussed herein.

Endoscopic surgical systems discussed herein have a number of advantages over existing saphenous vein-harvesting systems. For example, existing saphenous vein-harvesting systems do not include any suction functionality to clear the field of vision. If the field of view becomes covered with blood or debris, it needs to be removed. In some existing instruments, the field of vision may be cleared, for example, by irrigating the distal end by spraying liquid toward the endoscope (similar to windshield wiper fluid). However, the liquid pools in the extremity, potentially blocking/blurring the visual field.

Thus, with current systems, when there is bleeding or a pool of irrigation liquid (water, dirty saline, etc.) or debris (strands of tissue, adipose tissue, small blood clot, etc.) obstructing the visual field, the BTT must be deflated and removed and the entire endoscopic system needs to be removed from the extremity. The wound is irrigated from the incision site, blindly squirting irrigation solution into the wound. Then the contents (blood, debris, irrigation solution, etc.) are "milked" or rolled out by sequentially applying pressure externally (meaning on the skin from the outside), from the location of the distal end of the endoscope to the incision site (e.g., with a rolled up lap pad). The debris and liquid are expelled out through the incision site. If there is internal bleeding, for example, from a side branch of the vein, or a small artery is injured and bleeding, external pressure is held for a couple minutes to control hemostasis. Meanwhile, there is no direct vision as the endoscope has been removed. Time is spent removing and re-inserting the endoscopic device, and each time it is re-inserted, it goes back to a slightly different position. Thus, still more time is needed to re-situate/re-orient the device after re-insertion. In addition, even when anatomical landmarks are noted to mark the initial placement of the endoscopic device (e.g., vein branches, adipose tissue, a bifurcation of the vein, a narrowed area, a tissue bulge, obvious bleeding, artery branch protruding), when re-inserting the device, the wrong plane could be opened, which may cause tissue damage and open areas for fluid to accumulate, leading to seromas, hematomas, and poor wound healing.

With the suction device of the present invention as part of the endoscopic system, the operative field can be cleared quicker and a source of bleeding can be more easily identified/recognized/located. One can irrigate, suction, and then cauterize the bleeder by simply exchanging the suction device and the bisector device, all while keeping the endoscope and cannula in situ and maintaining direct visualization at all times.

Thus, it should be appreciated by those skilled in the art that having suction functionality in an endoscopic system makes minimally invasive endoscopic surgical procedures more time efficient, safer, and saves blood loss (e.g., loss of blood due to removing and re-inserting the instrumentation, the time it would take to irrigate then re-insert the endoscope, cannula, and bisector and find the previous area and the source of the bleeding). It further allows for continuous stability of the operative site. With suction, the irrigation liquid can be easily removed and not be a cause of visual obstruction.

Suction may be used with the smaller cannulas described above in connection with FIGS. 1C, 2B, and 5. Suction may also be used with existing and future endoscopic systems, such as an existing saphenous-vein harvesting system having a larger cannula, to augment/improve the functionality and solve the problem of blood/fluid obstruction in those systems as well. In such embodiments the suction device may be sized to extend the length of the cannula (e.g., 43 cm).

Another advantage of the endoscopic surgical systems discussed herein is maneuverability. Existing saphenous vein-harvesting systems can be unnecessarily large/cumbersome and awkward for certain cardiovascular harvesting procedures, such as radial artery harvesting (upper extremity; forearm/arm) and harvesting smaller saphenous vein segments (partial extremity).

Radial artery harvesting is used as a conduit for coronary artery bypass surgery. The radial artery is harvested from the distal area (wrist) to the antecubital (inside of elbow) proximal end. Once the radial artery is confirmed as a useable conduit, without compromising the arterial blood flow to the hand, the initial dissection is performed, identifying the radial artery with direct vision. The dissector (endoscope with the dissector tip) is introduced, separating the tissue surrounding the radial artery with bilateral vein attachments (small veins). The radial artery is separated anteriorly, posteriorly, laterally, and medially. Branches are isolated. The dissector is then exchanged for the endoscopic device (harvesting cannula and endoscope without dissector tip) with the bisector/bipolar device attachment. Branches are cauterized and cut. Any possible bleeding causes the field of vision to be covered very quickly as the arterial flow is pulsatile and under pressure. Suction allows for the blood to be removed. The bleeding is controlled and removed with harvesting cannula in situ. The suction is exchanged with the bisector. Once the radial artery and subsequent vein are free from surrounding tissue a separate stab site is made at the proximal end and the radial artery is ligated ahead of the brachial junction. The radial artery is then prepared by flushing with heparinized saline and all branches are secured. As described in detail below, the smaller device allows for more appropriate size suitability. The harvesting cannula with suction can be re-introduced and the prior radial artery donor site is inspected for any possible bleeders. The suction device allows for removal of irrigation solution to secure a hemostatic environment and then closure of the site distally. The proximal site can be closed prior to final inspection to allow for a $CO_2$ seal.

Typically, when harvesting a right radial artery the cardiac surgeon is standing at the right side of the patient's chest (the patient is lying on his/her back with arms straight out on arm boards in standard cardiac surgical procedures). The existing saphenous vein-harvesting cannula that may be used is long, and the radial artery from wrist to antecubital space (inside of elbow) is a much shorter distance. The larger cannula is hard to manage and difficult to balance with a narrow arm board. The smaller cannula described herein is more appropriately sized and can eliminate contamination and obstruction from close surroundings (e.g., a surgeon hitting instrumentation with his/her left arm; if the surgeon is harvesting the internal mammary artery at the same time the radial artery is being harvested, it is often the surgeon's back and left arm that are in the radial artery operative field with a high incident of hitting/contaminating). In some operating rooms, the cardio-pulmonary bypass machine (perfusion machine), which is bulky (bigger than the patient), is also at the patient's right side. Thus, there may be very little room on the patient's right side for the surgeon/harvester to access a right radial artery. The harvester may be in the surgeon's way; the surgeon may be in the harvester's way; inches away from both the surgeon and the person harvesting the radial artery is the cardio-pulmonary bypass machine, which is the life line to the patient. A shorter/smaller cannula device is more manageable and can help prevent/minimize the contamination that occurs when using a larger endoscopic device, and is therefore preferable for radial artery harvesting.

The smaller cannula described herein may be preferable in certain cases even for saphenous vein-harvesting, for which the larger endoscopic systems were designed. For example, sometimes the cardiac surgery only needs one or two pieces of saphenous vein, which can be taken from the lower leg or just a segment from the upper leg. If only a small segment is needed, then the smaller cannula would be better suited to use for harvesting (whereas if 4-5 segments are needed for bypass, an existing, larger cannula may be better suited). For example, when harvesting a segment of saphenous vein in the lower leg (e.g., the knee down), the endoscopic harvesting device often ends up resting in the chest area. Thus, a smaller device is more manageable. The patient might be a "re-op," meaning they had cardiac surgery before and are now returning for another cardiac bypass surgery and all that remains is the lower leg or only the upper thigh, so again the smaller cannula would be the better option. Another example is if a lesser saphenous vein is being harvested. Lesser saphenous veins are difficult to harvest with the large endoscopic system. The lesser saphenous veins are anatomically on the back side of the lower leg. The smaller cannula would be a better, more manageable option for this case as well.

The saphenous vein in the lower extremities can be harvested and used as a conduit for coronary artery bypass grafting. Once the saphenous vein is identified at the medial aspect of the knee area, the dissector (endoscope with dissector tip) is introduced through the blunt tip trocar (BTT). All tissue is separated from the vein, anteriorly, posteriorly, laterally and medially, isolating all branches. The dissector is then exchanged for the endoscopic device (harvesting cannula and endoscope without dissector tip) with the bisector/bipolar device attachment. Branches are cauterized and cut with the bisector. The grooves on the bisector handle allow for better handling and grip. A slight slip of the bisector while bovieing (cauterizing) can easily damage the donor saphenous vein, compromising the integrity of the vein. Any possible bleeding, irrigation fluid, and/or debris can be removed by the added suction device. Once all branches are isolated the vein can be removed at the proximal end through a separate stab incision. The vein is ligated under and removed. The stab site can be closed. The harvesting cannula can be re-introduced and the donor site of the saphenous vein is irrigated and the contents suctioned out. Any bleeding can be cauterized by exchanging the suction with the bisector. Once hemostasis is confirmed the endoscopic device is removed and the site is closed.

If more vein is required prior to ligating, the endoscope with dissector tip is flipped around and the knee (now considered the proximal end) is harvested down to the ankle. The same procedure is performed.

If only a lower leg segment is required, there is the option to start at the ankle and work most distally (ankle, medial fossa) to proximally (the medial aspect of the knee).

In harvesting from the knee to the ankle, the large endoscopic device and attachments/cords (camera, light source, bovie cord—the cauterizer, $CO_2$) all extend out the end of the harvesting device and can drape into the abdominal area and often fall in the chest area. This causes difficulty for the surgeon at the chest and cardio-pulmonary artery and venous lines. The operating area is cluttered, leading to increased chance of contamination. Thus for this case in particular, a smaller device of the embodiments described herein is more appropriate.

In harvesting both the radial artery and the saphenous vein, any incidental injury caused by the cauterizing because of slippage of the handle can damage the conduit, compromising the entire bypass surgery. The conduits become the blood flow to the heart, from the aorta to the distal aspect of the stenosis, bypassing the stenotic area. Thus, the non-slip features of the bisector/bipolar device handle 144, 544, 644 described herein, are of particular importance for these procedures.

Suction and irrigation allow for better visual comprehension and less chance of error.

Both conduits, a segment of saphenous vein and/or the radial artery(ies) used for coronary artery bypass surgery, should be in the best presentation in terms of integrity and structure. A smaller device allows for better manageability, and suction prevents the removal and re-insertion of the device, thus limiting the possibility of error and more dissection down a false plane looking for the original site.

These are exemplary benefits and uses of the endoscopic surgical devices/systems described herein, and should not be construed as limiting; other advantageous applications may easily be recognized by those of ordinary skill in the art.

Endoscopic AV Fistula Surgeries

The incidence and prevalence of end-stage renal disease continues to increase. Patients with end-stage renal disease require vascular access for dialysis. Some of these patients require temporary access while awaiting a kidney transplant (assuming they are an acceptable candidate), while others (e.g., those who are not transplant candidates) may require dialysis for the rest of their lives. Decisions about the type of dialysis and the best method of access for dialysis require collaboration among the patient, nephrologist, and access surgery team.

Primary autogenous arteriovenous (AV) fistulas are the preferred means of vascular access for hemodialysis. In patients who choose hemodialysis, an AV fistula is often created preemptively, allowing time for the fistula to mature pending usage. Indeed, the National Kidney Foundation Kidney Disease Outcomes Quality Initiative guidelines support a "fistula first" doctrine.

Traditional venous transpositions use an open technique generally as follows. If the anatomy permits, surgically created vascular access starts distally on the upper extremity. The radial-cephalic path is the most distal access option. In the upper arm, the brachial artery is anastomosed to either the basilic or cephalic veins. Initially, a deep cephalic-vein-to-brachial-artery fistula is created through a horizontal incision (e.g., 3 to 5 cm) near the antecubital fossa.

In many patients, the cephalic vein in the upper arm is superficial enough for direct cannulation for hemodialysis. After a period of maturation (e.g., four to six weeks), the AV fistula is assessed for palpable thrill, audible bruit, and the ability of the vein to be accessed through the skin for dialysis, which are indicators of a successful AV fistula. If necessary, ultrasound may be used to assess fistula size and depth.

If the vein (whether cephalic or basilic) remains too deep, the patient is scheduled for a second surgery for transposition. Vein transposition is also referred to as superficialization, as the vein is dissected from the deep tissue and embossed directly under the skin to allow easier access of the hemodialysis catheters. This is done through a separate vertical incision (referred to as the conventional open incision) from the antecubital fossa to the axillary area. Patients with deep veins or extensive adipose tissue typically require this two-stage surgery: the first stage completes artery and vein anastomosis (the fistula), and the second completes the transpositioning of the vein.

An open AV fistula transposition surgical incision is long (about 20 to 25 cm in length, from the antecubital space to the axillary area) and unsightly. Patients who undergo this conventional procedure are at risk for infections, bleeding, and painful surgical sites. Each surgical procedure lends itself to scarring and potential deformities. Many of these patients also have comorbidities, such as diabetes, predisposing them to poor wound healing. Renal-failure patients are at particularly high risk for complications from any surgery, and immunosuppressant therapy places kidney transplant recipients at even greater surgical risk.

Over time, chronic-renal-failure patients may require revisions or develop painful aneurysmal fistulas that necessitate removal of the AV fistula. An AV fistula may fail for various reasons, including low or poor blood flow, failure to mature, excessive pain (e.g., due to repeated dialysis needling), a sclerotic vein, and/or a thrombotic vein. Failure can be disheartening to a patient who realizes that another surgery is required. In addition, patients with functioning renal allografts (post-renal transplant) frequently request fistula removal, as these fistulas can be painful, disfiguring, and a reminder of the patient's experience on hemodialysis. Traditionally, these ligations and excisions are completed through incisions that extend the length of the aneurysmal fistula, which also carry a risk of infection, bleeding, painful surgical sites, and scarring.

The minimally invasive endoscopic methods and systems described here provide an alternative approach for AV fistula creation/transposition and ligation/excision.

The novel minimally invasive endoscopic surgical methods discussed herein include: (i) harvesting of a deep basilic or cephalic vein for creation of a brachial-basilic or brachial-cephalic AV fistula, with simultaneous transpositioning; (ii) harvesting of a deep basilic or cephalic vein for transposition of an existing brachial-basilic or brachial-cephalic AV fistula; and (iii) ligating and excising an aneurysmal radial-cephalic, brachial-cephalic, or brachial-basilic AV fistula from the upper or lower arm. As will be appreciated by those of skill in the art, although surgical procedures may be performed with any number of endoscopic devices, the devices and systems disclosed herein with regard to FIGS. 1-6 are particularly well suited for performing such procedures.

In certain embodiments, the harvested vein is transpositioned to directly under the skin, then anastomosed to the brachial artery, creating an AV fistula accessible for hemodialysis. This replaces the traditional two-stage surgery with a single-stage surgery and eliminates the long vertical incision associated with a conventional open AV fistula transposition.

In other embodiments, an aneurysmal AV fistula is ligated and excised endoscopically, thereby minimizing incisions.

As compared to traditional open AV fistula surgeries, these procedures reduce body disfigurement, scarring, postoperative pain, and potential for infection. Following the procedure disclosed herein to harvest a deep upper-arm cephalic vein, for example, the patient is left with only two small scars. This procedure also eliminates repeated or staged surgery and promotes faster recovery and improved wound healing and patient body image. These procedures are described in greater detail below.

I. Primary Creation with Simultaneous Endoscopic Transposition of Upper Extremity Basilic or Cephalic Vein for Arterial Venous Fistula In some embodiments, an exemplary method for primary AV fistula creation with simultaneous endoscopic transposition of an upper extremity basilic or cephalic vein is as follows. A 2-cm incision is made at the antecubital area. The artery and intended vein are identified. A blunt tip trocar (BTT) is introduced to the incision. A balloon on the BTT is inflated to create a seal, and low pressure $CO_2$ insufflation is started. An endoscopic device (endoscope and cannula) is introduced through the BTT. The endoscope is advanced with a conical tip for dissection. The vein is passed superiorly, inferiorly, medially, and laterally, and vein branches are isolated. The C-ring at the end of the cannula is exchanged for (e.g., retracted) and replaced with a bisector/bipolar device, which is advanced through the cannula. The vein branches are cauterized and cut/bisected. A 1-cm stab site is made at a proximal end of the vein (axillary area). The vein is grasped and pulled out through the stab site. The bisector/bipolar device is removed, and the vein is cannulated and flushed with heparanized saline. The cauterized side branches of the transpositioned vein are tied off/reinforced (e.g., with 4-0 silk ties). A tunneler device is passed from the distal to the proximal incision. The vein is loaded into the tunneler. The tunneler is passed with the vein from the proximal to the distal incision. Vascular clamps are applied. The vein is anastomosed to the artery end. Vascular clamps are removed. The resulting AV fistula is assessed for thrill, which indicates a successful AV fistula creation. The incision sites are closed.

II. Endoscopic Staged Transposition of Upper Extremity Cephalic Vein for Arterial Venous Fistula In some embodiments, an exemplary method for endoscopic staged transposition of an upper extremity cephalic vein for an AV fistula is as follows. A 2-cm incision is made through the primary incision (made when the AV fistula was initially created) at the antecubital area. The AV fistula is identified and isolated. A vascular clamp is placed above the anastomosis on the vein. A cut is made on the vein side and the vein edge is secured with silk tie. The silk ties are clamped or tacked to a drape so as not to drag the vein into the wound. A BTT is introduced to the incision. A balloon on the BTT is inflated to create a seal, and low pressure $CO_2$ insufflation is started. An endoscopic device is introduced through the BTT. The endoscope is advanced with a conical tip for dissection. The vein, which may be within deep layers of adipose tissue, is passed superiorly, inferiorly, medially, and laterally, and vein branches are isolated. The C-ring is exchanged for (e.g., refracted) and replaced with a bisector/bipolar device, which is advanced through the cannula. The vein branches are cauterized and cut/bisected. A 1-cm stab site is made at a proximal end of the vein (axillary area). The vein is grasped and pulled out through the stab site. The bisector is removed and the vein is cannulated and flushed with heparanized saline. The cauterized side branches of the transpositioned vein are tied off/reinforced (e.g., with 4-0 silk ties). A tunneler device is passed from the distal to the proximal incision. The vein is loaded into the tunneler. The tunneler is passed with the vein from the proximal to the distal incision. Vascular clamps are applied. The vein is re-anastomosed, vein to vein-artery (AV fistula site) end to end. Vascular clamps are removed. The resulting AV fistula is assessed for thrill, which indicates a successful AV fistula creation. The incision sites are closed.

III. Endoscopic Excision of an Aneurysmal Arterial Venous Fistula in the Upper Extremity (Radial-Cephalic, Brachial-Cephalic, or Brachial-Basilic)

In some embodiments, an exemplary method for endoscopic excision of an aneurysmal AV fistula in the upper extremity (radial-cephalic, brachial-cephalic, or brachial-basilic) is as follows. A 2-cm incision is made through an existing scar from the initial creation of the AV fistula. The anastomosis of the artery and vein is identified and isolated. A vascular clamp is placed on the vein side of the anastomosis. The vein is divided from the anastomosis. The arterial stub is over-sewn. The first couple of centimeters of vein are dissected out. Blood is expressed from the vein lumen. The vein edge is tied, preferably twice, with 2-0 silk tie. The silk ties are tacked to a drape so as not to drag the vein into the wound. A BTT is introduced to the incision. A balloon on the BTT is inflated and low pressure $CO_2$ insufflation is started. An endoscopic device is introduced through the BTT. The endoscope is advanced with a conical tip for dissection. The vein is passed superiorly, inferiorly, medially, and laterally, and vein branches are isolated. The C-ring is exchanged for (e.g., retracted) and replaced with a bisector, which is advanced through the cannula. A 1-cm stab site is made at a proximal end of the aneurysmal vein. The vein is grasped and a vascular clamp is placed around the vein. The vein is excised and the vein specimen is removed. The proximal vein stub is over-sewn, and the proximal clamp is removed. The wound is irrigated with antibiotic solution. Incisions are closed (e.g., with 3-0 vicryl then 4-0 biosyn). Dressings are applied and the extremity is wrapped (e.g., with ACE™ wrap). The wrap is preferably left on for 24 hours unless the patient has finger numbness, pain, or finger swelling, and the extremity is preferably kept elevated. Heavy lifting is not recommended.

As will be appreciated by those of skill in the art, the foregoing procedures are exemplary, and procedures including fewer or additional steps, or performing such steps in a modified order, or other variations are also within the scope of the present invention. For example, for each of the above procedures, a block with Monitored Anesthesia Care (MAC) may be used unless the patient is under general anesthesia. Also, in some embodiments, transpositioning does not include a second stab-grab incision.

In some embodiments, a tunnel is created through adipose tissue with the cannula, eliminating any use of a separate tunneler device. After the vein is pulled out at the proximal end, flushed with heparinized saline, and inspected/examined for leaks, the branches are tied off. Then, instead of using the tunneler device, the endoscope with dissector tip is passed through, distal to proximal (in the same fashion that tunneling is performed with the tunneler device), just under the skin, making a tunnel. Then the endoscope with dissector tip is withdrawn and replaced with the endoscopic device (harvesting cannula and endoscope with dissector tip removed) with bisector/bipolar device attachment. The bisector is advanced through from distal to proximal following the same subcutaneous path. Once the bisector is through to the proximal end, there is a tiny opening on the C-ring to thread a suture. The end of the suture is tied to the vein, then pulled through the endoscopic device, carefully advancing the vein through under the skin. Preferably there are no clips, just suture ties used on the vein. These embodiments eliminate the use of a separate tunneler instrument for transpositioning, making the procedures entirely endoscopic except for the anastomosis (sewing the vein end to the side of the artery), which is typically performed under direct vision at the incision site.

Endoscopic Fasciotomy Surgeries

Compartment syndrome is a limb threatening condition which can be found wherever a compartment can be anatomically present. This includes, for example, the hand, forearm, upper arm, abdomen, buttock, and lower extremities (both upper and lower legs as well as the feet). Compartment syndrome can occur when the muscle compartment exceeds the perfusion pressure of the tissue. The fascia covering creates a restrictive element, thereby inhibiting any expansion of the affected anatomical area. Compartment syndrome is the compression of underlying tissue, vascular compression and/or occlusion, nerve damage, muscle compression and restriction, leading to tissue ischemia and necrosis.

Compartment syndrome can be caused, for example, by long bone fractures, burns (chemical, thermal, and/or electrical), bleeding in enclosed spaces, external or crush injuries/events, envenomation from snake bites, thrombotic or embolic events (e.g., deep vein thrombosis), traumatic injuries, exercise, prolonged extremity immobilization, vascular injury, massive fluid resuscitation in burn or trauma victims, and/or morbid obesity. Compartment syndrome can be chronic in certain athletes from exercise-induced or repetitive impact injuries.

A fasciotomy is the treatment for compartment syndrome. The fasciotomy is performed to relieve underlying tissue pressure, and enable better perfusion and blood flow. A fasciotomy is performed to prevent tissue death. The fascia tissue can vary in terms of density, thickness, and elasticity.

Traditional fasciotomies are open fasciotomies that involve long incisions made longitudinally from proximal to distal through the skin and tissue to the internal fascia of the affected area. Thus, an open fasciotomy can be a source of morbidity and lead to potential infections due to exposed underlying tissue, poor wound healing, skin grafts, disfigurement and extensive scarring, and decreased and/or permanent functional impairment.

Such issues with traditional fasciotomies due to compartment syndrome have left orthopedic surgeons looking for a better method to decompress the tissue without making large incisions. Other current methods include "semi-blind" passage of long scissors to cut the fascia and the use of army-navy retractors, in chronic compartment syndrome patients. Nothing is known to have been attempted on acute compartment syndrome patients. Problems with the existing semi-blind techniques include potential risk for incomplete fascia division, nerve injury/impingement, and/or unrecognized fascial defects.

In addition, because there is no "designated" device or appropriate instrument to use for fasciotomy procedures, orthopedic surgeons have attempted various alternative techniques. For example, some have used a gynecological speculum (the instrument that is used for obtaining a PAP smear for women), whereas others have used a shoulder arthroscope (a scope for the shoulder). Use of various instruments intended for other procedures demonstrate that there is a need and a setting for improved methods and devices for performing fasciotomies.

Once a fasciotomy has been determined to be the surgical intervention, the option of performing the procedure endoscopically can be considered. Embodiments of the present invention provide endoscopic fasciotomy procedures that may be easily completed for preventing or treating compartment syndrome. Instead of opening a leg or arm through the traditional open incision, such procedures can be performed through a smaller incision, while providing complete visualization. Endoscopic fasciotomy may be useful, for example, in situations where transport to a higher level of trauma facility may be needed and endoscopic fasciotomy could provide an initial intervention. More generally, the endoscopic fasciotomy approach of the present invention may be useful in situations in which there is a need for space for swelling, but an open technique would increase morbidity.

Thus, embodiments of the minimally invasive endoscopic surgical methods of the invention further include, for example: (iv) endoscopic leg fasciotomy and (v) endoscopic arm fasciotomy. These procedures are described in greater detail below.

Fundamental knowledge of the anatomy and the underlying tissue, as well as the anatomical landmarks and structures, is assumed for these procedures (including the fascia and muscles, as well as the nerves and vascular tissue). Briefly, each lower leg has four muscle compartments (anterior, lateral, superficial posterior, deep posterior). The thigh has four compartments (anterior, medical, lateral and posterior). The buttock is composed of three major muscles, each within its own compartment, the gluteus maximus muscle, gluteus medius muscle, and the gluteus minimus muscle. The upper arm has two compartments, anterior and posterior. The forearm has two compartments, anterior and posterior.

IV. Endoscopic Leg Fasciotomy

In some embodiments, an exemplary method for endoscopic leg fasciotomy is as follows. An initial incision is made approximately 2 cm above the most proximal site. The tissue is then dissected down to the fascia. Once enough space is created then the endoscopic device is inserted. Once identifying tissue is clearly visualized, then the endoscopic dissector (endoscope with dissector tip) is advanced longitudinally to the desired distal site. Once enough space has been created (e.g., tissue plane dissected) then the dissector tip is removed (e.g., unscrewed) and the endoscopic device (harvesting cannula and endoscope without dissector tip) with the bisector/bipolar device attachment is inserted. Appropriate landmarks (such as muscles, nerves, and connective tissue of the fascia) should be identified. The bisector/bipolar device penetrates the fascia, cauterizing enough to make an initial opening of approximately 3 mm. The C-ring cups or grasps the edge of the fascia, which is preferably lifted off of the underlying tissue, vascular structures, muscle, and nerves. As the C-ring creates a counter tension at the crotch of the fascia opening, the bisector/bipolar device is advanced, cauterizing and cutting the fascia. As the bisector/bipolar device is advanced, care is taken to maintain hemostasis. Suction can be applied by exchanging the bisector/bipolar device with the suction device, as described herein.

Once the fascia is opened, then the endoscopic device is retracted to the insertion site and slowly advanced for inspection and then to separate individual muscle groups as needed. The procedure is repeated for as many compartments of fascia as are necessary to be opened.

In performing a fasciotomy of the thigh/upper leg, for example, the 2-cm incision may be at a site near the buttock with the endoscopic fasciotomy proceeding along the femur toward the knee. In the lower leg, the 2 cm incision may, for example, be at a site near the knee (lateral or medial) with the endoscopic fasciotomy proceeding along the tibia/fibula toward the lateral/medial malleolus.

V. Endoscopic Arm Fasciotomy

In some embodiments, an exemplary method for endoscopic arm fasciotomy is as follows. An initial incision is made approximately 2 cm in length at the most proximal area. Dissection to the fascia is obtained. The endoscopic device is inserted into the incision and the dissector tip creates an open plane as it is advanced to the distal site. The dissector tip is then removed and the endoscopic device (harvesting cannula and endoscope without dissector tip) with the bisector/bipolar device attachment is inserted. Once the fascia is clearly identified, a small opening, approximately 3 mm (enough to open the fascia for the bisector to be advanced) is created. As with the leg fasciotomy, the fascia is cupped by or grasped with the C-ring, creating counter tension. Then the bisector/bipolar device is advanced in synchrony with the harvesting cannula, cauterizing the fascia while cutting it open. Once the distal area is reached, then the bisector/bipolar device is withdrawn. If further areas of the fascia need to be cut, then the endoscopic device is retracted to the insertion site and the same procedure is applied.

Each of the above fasciotomy procedures is typically performed in the operating room; however, if properly prepared and if equipment is available, fasciotomies can be performed in the emergency room. These endoscopic procedures can be performed under a regional block anesthesia or general anesthesia, taking into consideration the presenting situation.

Each fasciotomy allows room for swelling and expansion of the underlying tissue. Assessment of the tissue for perfusion, pallor, pain, pulses, and/or paresthesia is preferably performed. If more extensive expansion is required then the endoscopic fasciotomy may be converted to an open fasciotomy, or an open fasciotomy may be performed following the endoscopic fasciotomy.

An appropriately sized endoscopic system with suction, such as that described herein, is preferred for these minimally invasive endoscopic fasciotomy surgeries, allowing for complete visualization, minimizing potential internal damage, and permitting the best possible outcomes. However, an existing endoscopic device, such as a saphenous vein-harvesting device, may also be used for the fasciotomy procedures as described above.

Additional uses of the minimally invasive approach described herein are also contemplated, particularly for any endoscopic surgical procedures in which small incisions are desirable. The smaller endoscopic system described herein may be more appropriately sized, easier for the harvester to use, and may minimize error.

EXAMPLES

The invented surgical methods presented herein are further described in the following examples, which do not limit the scope of the invention set forth in the claims. The following examples describe clinical cases that have been treated according to some embodiments of the invented methods. The surgeries described in the examples were performed using an existing saphenous vein-harvesting system. However, in some embodiments (such as those in the upper extremities), an improved endoscopic system such as that described above, which is smaller, more precise, and easier to use, is preferred for these surgical methods.

Example 1: Transposition and Creation of Brachial-Cephalic AV Fistula with Endoscopic Vein Harvesting The initial antecubital fossa incision was about 2 cm in length. Once the brachial artery and the cephalic vein were identified, an endoscopic device was introduced through the same incision and utilized to harvest the cephalic vein from the most distal to proximal end.

The endoscopic device was equipped with in-line tools. With the conical tip attached to a 7-mm scope, the cephalic vein was followed on a level plane. Insufflation with low-pressure $CO_2$ created a visual field that enabled the identification of vein branches. The branches were cauterized with a bisector tip providing hemostatic control. Harvesting included dissection of adipose tissue from the vein and avoidance of the nerve as it was visualized. The concave shape of the endoscope's C-ring basined the vein, allowing the surgeon to run the vein from its proximal to distal end while inspecting for any further dissection. This also allowed for careful assessment to ensure all branches had been ligated and divided.

A 2-cm counter-stab incision was then made at the proximal end to allow for the vein to be reined out. The vein was inspected and flushed with heparinized saline. Divided venous-side branches were reinforced with 4-0 silk ties. The patency of the vein was evident. A standard AV graft tunneling device was used to tunnel the vein from the proximal to the distal incision in the subcutaneous plane. The harvested vein was placed in the inner aspect of the tunneler and passed back through from the proximal end to the distal incision. The transpositioned vein was then anastomised to the side of the brachial artery. Venous and arterial clamps were removed; a palpable thrill was appreciated. Hemostasis was obtained, and the incisions were closed using absorbable sutures. The need for a second surgery was eliminated. At eight weeks, the fistula was mature and able to be cannulated for hemodialysis.

Example 2: Transposition of Brachial-Basilic AV Fistula with Endoscopic Vein Harvesting The patient presented with a brachial-basilic AV fistula in situ that, while adequate in size, was too deep for hemodialysis needle puncture access. The patient was morbidly obese, had comorbidities that would delay wound healing, and was at risk for complications. The minimally invasive approach to endoscopic harvesting of the basilic vein ensued.

The antecubital incision from the creation of the AV fistula was opened and the anastomosis site identified. The arterial flow was clamped on the venous side. An endoscopic device was introduced and the undistended deep basilic vein harvested. A 2-cm counterincision was made about 17 cm from the insertion site at the proximal side. The basilic vein was reined out and all branches were ligated. After patency had been established, the basilic vein was tunneled back through the subcutaneous plane. The transpositioned vein was re-anastomised back to the original AV fistula site. Venous and arterial clamps were removed; a palpable thrill was appreciated.

When the patient returned for a two-week post-operative follow up, the vein was palpable throughout with a thrill and the incisions were well-healed. The patient was instructed to return in four weeks for AV fistula anastomosis maturation assessment.

Example 3: Radial-Cephalic AV Fistula Ligation and Excision

The patient had a renal transplant and complained of an unsightly and painful radial-cephalic AV fistula. A 2-cm incision was made through the original fistula-creation scar. The radial-cephalic AV fistula anastomosis was dissected and ligated, halting the arterial blood supply. An endoscopic device was introduced through the same incision. The conical tip was used to separate the thickened fistulous vein from surrounding tissue. Insufflation with $CO_2$ was used to create a visual field. All identifiable branches were cauterized and bisected. A 2-cm stab incision was made approximately 15 cm from the distal incision. The aneurysmal vein was reined out through the stab-site incision and tied off. The incisions were irrigated and closed. An ACE™ wrap was placed over the site for 24 hours with instructions to remove if any numbness or tingling in the fingers occurred.

The patient returned approximately one week later. There was no report of any numbness or tingling in the fingers and no swelling. Distal pulses were intact, as was distal perfusion.

Example 4: Brachial-Cephalic AV Fistula Ligation and Excision

The patient had a renal transplant and complained of an unsightly and painful brachial-cephalic AV fistula. As in Example 2, the incision was established through the original creation-site scar at the antecubital fossa. The cephalic vein was ligated near the arterial anastomosis and the aneurysmal cephalic vein harvested endoscopically. A counterincision was made at the proximal end approximately 15 cm from the distal site. The vein was reined out through a 1-cm incision, tied off, and excised. The wound was irrigated and closed. An ACE™ wrap was applied. Two weeks later, the patient had minimal swelling and no complaints of any pain or discomfort. Distal pulses and perfusion were intact.

While there have been shown and described fundamental novel features of the invention as applied to the preferred and exemplary embodiments thereof, it will be understood that omissions and substitutions and changes in the form and details of the disclosed methods, devices, and systems may be made by those skilled in the art without departing from the spirit of the invention. Moreover, as is readily apparent, numerous modifications and changes may readily occur to those skilled in the art. Hence, it is not desired to limit the invention to the exact construction, procedures, and operations shown and described and, accordingly, all suitable modification equivalents may be resorted to falling within the scope of the invention as claimed. It is the intention, therefore, to be limited only as indicated by the scope of the claims appended hereto.

What is claimed is:

1. A method of endoscopically harvesting at least a one section of a blood vessel from an extremity or partial extremity, the method comprising:
    making an incision in the extremity at one end of the at least one section of blood vessel, the incision sized to receive an endoscopic device;
    introducing an endoscope through the incision, the endoscope having a dissector tip, and dissecting tissue around blood vessel using the tip;
    withdrawing the endoscope from the incision;
    introducing the endoscopic device through the incision, the endoscopic device configured with a harvesting cannula having a first endoscope port, a second insert port, a handle at a proximal end and a shaft extending from the handle to a distal end, the shaft having a length of about 20 cm to about 26 cm the shaft defining a chamber configured to receive at least one of a portion of a device inserted in the first endoscope port and at least a portion of a device inserted the second insert port; and a bisector/bipolar device provided in the second insert port;
    severing branches of the blood vessel under endoscopic visualization using the bisector/bipolar device;
    after severing the branches, withdrawing the bisector/bipolar device from the second insert port and inserting a suction device having a distal end into the second insert port so that the distal end is proximate to a visual field of the endoscope; and
    activating suction through the suction device and clearing the visual field;
    after clearing the visual field, withdrawing the suction device from the second insert port and inserting the bisector bipolar device into the second insert port;
    ligating the blood vessel;
    making a stab incision at the other end of the at least one section of blood vessel;
    and harvesting the at least one section of blood vessel through the stab incision.

2. The method of claim 1, wherein the blood vessel is a radial artery in the forearm.

3. The method of claim 1, wherein the blood vessel is a saphenous vein in the lower leg below the knee.

4. The method of claim 3, wherein, the blood vessel is a lesser saphenous vein on the back side of the lower leg.

5. The method of claim 1, wherein the blood vessel comprises one or two sections of saphenous vein in the upper thigh.

6. The method of claim 5, wherein the incision is made at the knee and stab incision is made in the upper thigh.

7. The method of claim 6, wherein an additional length of blood vessel is obtained by harvesting the saphenous vein from the knee to the ankle.

8. The method of claim 3, wherein the incision is made at the knee and the stab incision is made at the ankle.

9. The method of claim 3, wherein the incision is made at the ankle and the stab incisions is made at the knee.

10. The method of claim 1, wherein the shaft has a length of about 23 cm.

11. The method of claim 1, further comprising:
    introducing irrigation fluid;
    activating the suction through the suction device, and removing the irrigation fluid.

12. The method of claim 1, wherein the body of the suction device has a length about 29 cm to 35 cm.

13. The method of claim 1, wherein the body of the suction device has a length of about 32 cm.

14. The method of claim 1, wherein the body of the suction device includes an additional length at the distal end that is fenestrated.

15. The method of claim 14 wherein the additional length at the distal end of the body of the suction device that is fenestrated is about 2 cm.

16. The method of claim 1, wherein the suction device is inserted into the harvesting cannula through the second insert port.

* * * * *